United States Patent
Schoepgens et al.

(10) Patent No.: US 10,493,010 B2
(45) Date of Patent: *Dec. 3, 2019

(54) REDUCTIVE COLOR REMOVAL USING SULFINIC ACID DERIVATIVES IN PASTE

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,560

(22) Filed: Nov. 10, 2016

(65) Prior Publication Data
US 2017/0128342 A1 May 11, 2017

(30) Foreign Application Priority Data
Nov. 11, 2015 (DE) .................. 10 2015 222 216

(51) Int. Cl.
*A61K 8/46* (2006.01)
*A61K 8/31* (2006.01)
*A61Q 5/08* (2006.01)
*B65D 81/32* (2006.01)

(52) U.S. Cl.
CPC .................. *A61K 8/46* (2013.01); *A61K 8/31* (2013.01); *A61Q 5/08* (2013.01); *B65D 81/32* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 5,776,240 A | 7/1998 | Deller et al. | |
| 6,171,347 B1 * | 1/2001 | Kunz | C11D 3/38654 132/208 |
| 6,319,288 B1 | 11/2001 | Jakob et al. | |
| 6,730,132 B1 | 5/2004 | Beckmann et al. | |
| 7,332,466 B2 | 2/2008 | Schmid et al. | |
| 2005/0130865 A1 | 6/2005 | Schmid et al. | |
| 2009/0276964 A1 | 11/2009 | Asada | |
| 2017/0112743 A1 | 4/2017 | Schoepgens et al. | |

FOREIGN PATENT DOCUMENTS

| | | |
|---|---|---|
| CN | 101390819 A | 3/2009 |
| DE | 3831098 A1 | 3/1990 |
| DE | 19710154 A1 | 9/1998 |
| EP | 0615018 A1 | 9/1994 |
| EP | 1300136 A2 | 4/2003 |
| GB | 1170133 A | 11/1969 |
| WO | 03037287 A1 | 5/2003 |
| WO | 2008055756 A1 | 5/2008 |
| WO | 2010063533 A1 | 6/2010 |
| WO | 2012/069599 A2 | 5/2012 |
| WO | 2013/017862 A2 | 2/2013 |
| WO | 2014/174230 A2 | 10/2014 |
| WO | 2016005143 A1 | 1/2016 |

OTHER PUBLICATIONS

UKIPO Combined Search & Examination Report GB 1618977.1 Completed: Sep. 1, 2017 dated Sep. 4, 2017 6 pages.
UKIPO Combined Search & Examination Report GB 1618975.5 Completed: Sep. 15, 2017 dated Sep. 18, 2017 6 pages.
UKIPO Combined Search & Examination Report GB 1708979.8 Completed: Feb. 27, 2018 dated Feb. 28, 2018 7 pages.
WebQC.org Chemical Portal. "pH Calculator—Calculates pH of a Solution". <https://www.webqc.org/phsolver.php>. Originally accessed Jun. 13, 2018 (Year: 2018).

* cited by examiner

*Primary Examiner* — Nicole P Babson
(74) *Attorney, Agent, or Firm* — James J. Cummings

(57) ABSTRACT

A multicomponent packaging unit (kit-of-parts) for reductive decoloration of colored keratin fibers includes, presented separately from one another,
    a container (A) containing a cosmetic agent (a) and
    a container (B) containing a cosmetic agent (b). The agent
    (a) in container (A)
      (a1) includes one or more sulfinic acid derivatives from a particular group,
      (a2) includes one or more fatty constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils,
      (a3) has a water content of at most 10.0% by weight, based on the total weight of the agent (a),
    the agent (b) in container (B)
      (b1) has a water content of at least 30.0% by weight, based on the total weight of the agent (b).
Also, a method is for reductive decoloration of colored keratin fibers using the multicomponent packaging unit.

14 Claims, No Drawings

REDUCTIVE COLOR REMOVAL USING SULFINIC ACID DERIVATIVES IN PASTE

FIELD OF THE INVENTION

The present invention generally relates to multicomponent packaging units (kit-of-parts) for reductive decoloration of colored keratin fibers, which include separately presented containers (A) and (B).

BACKGROUND OF THE INVENTION

Preparations for tinting and coloring hair are an important type of cosmetic agent. They can be used to lighten or darken the natural hair color according to the wishes of the individual in question, to achieve a completely different hair color or to cover unwanted color tones, such as gray tones for example. Conventional hair coloring agents are formulated either on the basis of oxidation dyes or on the basis of substantive dyes, depending on the desired color and permanence. Combinations of oxidation dyes and substantive dyes are also often used to achieve special shades.

Coloring agents based on oxidation dyes lead to bright and permanent color tones. However, they require the use of strong oxidizing agents, such as hydrogen peroxide solutions for example. Such coloring agents contain oxidation dye precursors, so-called developer components and coupler components. Under the effect of oxidizing agents or oxygen in the air, the developer components form the actual dyes in conjunction with one another or by coupling to one or more coupler components.

Coloring agents based on substantive dyes are often used for temporary coloring. The substantive dyes are dye molecules which are absorbed directly onto the hair and require no oxidative process for developing the color. Important representatives of this class of dyes include for example triphenylmethane dyes, azo dyes, anthraquinone dyes or nitrobenzene dyes, each of which may have cationic or anionic groups.

In all these coloring processes, it may happen that the coloring is to be completely or partially reversed for various reasons. A partial removal of the color may be advisable for example if the color result on the fibers turns out to be darker than desired. On the other hand, a complete removal of the color may also be desired in some cases. For example, it is conceivable that the hair is to be colored or tinted in a particular shade for a specific event, and the original color is to be restored after a few days.

Various agents and methods for color removal are already known in the literature. One method for color reversal which is well known from the prior art is the oxidative decoloration of the colored hair, for example using a conventional bleaching agent. In this process, however, the fibers may be damaged due to the use of strong oxidizing agents.

Furthermore, reductive processes for color removal have also already been described. For example, European patent application EP 1300136 A2 discloses hair treatment methods in which the hair is colored in a first step and is reductively decolored again in a second step. The reductive decoloration takes place in this case by applying a formulation containing a dithionite salt and a surfactant. In WO 2008/055756 A2, the reductive decoloration of keratin fibers is carried out using a mixture of a reducing agent and an absorbent.

In documents WO 2012/069599, WO 2014/174230 and WO 2013/017862, various sulfinic acid derivatives are described in agents for reductively removing color from colored hair. However, the presentation form and decoloration result of the agents described in said documents cannot yet be referred to as optimal.

When using reductive decoloring agents, the decoloration takes place by reduction of the dyes on the keratin fibers or hair. Through the reduction, the dyes are usually converted into their reduced leuco forms. During this procedure, the double bonds present in the dyes are reduced, the chromophoric system of the dyes is in this way interrupted, and the dye is transformed into a colorless form.

For reducing the dyes, usually strong reducing agents must be used which may enter into undesired reactions with oxidizing agents, such as oxygen in the air for example. In aqueous solution, the reducing agents are moreover often not very stable and are broken down at greater or lesser speed depending on the pH of the solution. For example, the reductive decoloring agent sodium dithionite, which is known from the prior art, is sensitive to atmospheric oxygen and slowly breaks down in aqueous solution. By increasing the pH, these breakdown reactions can be delayed. Adjustment to a weakly alkaline pH stabilizes aqueous dithionite solutions, so that the solution can be stored for several weeks to months if oxygen is excluded. However, if the reductive decoloring agents are to be stored for longer, if the exclusion of air cannot be reliably ensured or if high temperatures prevail under storage conditions, then presentation in solution, in particular in a water-containing solution, is not the method of choice. In order to circumvent this problem, often the reducing agents themselves are used as a solid, for example in powder form, in the prior art documents. However, this procedure is associated with various disadvantages.

The reducing agents must be dissolved in a cosmetic carrier before being applied. If, in this regard, they are incorporated in pure form, for example as a powder, in the cosmetic carrier, dust may arise which, if inhaled, may irritate the user's airways. If the particle sizes of the pulverulent reducing agent are selected to be larger, there is the risk that the reducing agents will not sufficiently dissolve and thus may lead to an uneven, unattractive decoloration result. If not fully dissolved, the reducing agent is also not fully available for the decoloring process, so that the decoloration result may in this case turn out to be weaker than planned.

If the solubility of the particulate reducing agent in the cosmetic carrier is poor, the user is moreover forced to mix together the solid reducing agent and the cosmetic carrier for a very long time. For the user, this procedure is inconvenient, time-consuming and therefore largely undesirable.

It is therefore desirable to provide a decoloring agent for decoloring colored keratin fibers, which decolors colored keratin fibers as evenly and as effectively as possible. The decoloring agent should have a high degree of storage stability and a good decoloring performance even after long storage periods at high temperatures. The ready-to-use decoloring agent should be easily prepared and conveniently applied by the user. In particular, no dust should arise during application. In addition, the consistency of the decoloring agent should be optimized so that on the one hand it can be easily applied to and distributed on the head of the user, but on the other hand does not drip down from the keratin fibers. Finally, the decoloring effect should be improved in comparison to the decoloring agents known from the prior art.

Furthermore, other desirable features and characteristics of the present invention will become apparent from the subsequent detailed description of the invention and the appended claims, taken in conjunction with this background of the invention.

BRIEF SUMMARY OF THE INVENTION

A multicomponent packaging unit (kit-of-parts) for reductive decoloration of colored keratin fibers includes, presented separately from one another, a container (A) containing a cosmetic agent (a), and a container (B) containing a cosmetic agent (b), wherein the agent (a) in container (A) includes one or more sulfinic acid derivatives from the group consisting of $(H_2N)(NH)C(SO_2H)$, formamidinesulfinic acid; $HN(CH_2SO_2Na)_2$, disodium [(sulfinatomethyl)amino]methanesulfinate; $HN(CH_2SO_2K)_2$, dipotassium [(sulfinatomethyl)amino]methanesulfinate; $HN(CH_2SO_2H)_2$, [(sulfinomethyl)amino]methanesulfinic acid; $N(CH_2SO_2Na)_3$, trisodium [bis(sulfinatomethyl)amino]methanesulfinate; $N(CH_2SO_2K)_3$, tripotassium [bis(sulfinatomethyl)amino]methanesulfinate; $N(CH_2SO_2H)_3$, [bis(sulfinomethyl)amino]methanesulfinic acid; $H_2NCH(CH_3)SO_2Na$, sodium 1-aminoethane-1-sulfinate; $H_2NCH(CH_3)SO_2K$, potassium 1-aminoethane-1-sulfinate; $H_2NCH(CH_3)SO_2H$, 1-aminoethane-1-sulfinic acid; $HN(CH(CH_3)SO_2Na)_2$, disodium 1-[(1-sulfinatoethyl)amino]ethane-1-sulfinate; $HN(CH(CH_3)SO_2K)_2$, dipotassium 1-[(1-sulfinatoethyl)amino]ethane-1-sulfinate; $HN(CH(CH_3)SO_2H)_2$, 1-[(1-sulfinoethyl)amino]ethane-1-sulfinic acid; $N(CH(CH_3)SO_2Na)_3$, trisodium 1-[bis(1-sulfinatoethyl)amino]ethane-1-sulfinate; $N(CH(CH_3)SO_2K)_3$, tripotassium 1-[bis(1-sulfinatoethyl)amino]ethane-1-sulfinate; and/or $N(CH(CH_3)SO_2H)_3$, 1-[bis(1-sulfinoethyl)amino]ethane-1-sulfinic acid; contains one or more fatty constituents from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils; has a water content of at most 10.0% by weight, based on the total weight of the agent (a), the agent (b) in container (B); and has a water content of at least 30.0% by weight, based on the total weight of the agent (b).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has surprisingly now been found that the aforementioned objects can be brilliantly solved if the reductive decoloring agent is presented as a multicomponent packaging unit (kit-of-parts) which includes two separately presented containers (A) and (B), wherein the containers (A) and (B) respectively include the cosmetic agents (a) and (b). The agent (a) includes at least one sulfinic acid derivative, which is selected from the representatives of a specific group, and one or more fatty constituents. The agent (a) is presented in substantially anhydrous form. The agent (b) is a water-containing cosmetic carrier. For the reductive decoloration of colored keratin fibers, the user mixes the agents (a) and (b) shortly before application and in this way prepares the ready-to-use decoloring agent.

A first subject matter of the present invention is a multicomponent packaging unit (kit-of-parts) for reductive decoloration of colored keratin fibers, which comprises, presented separately from one another, a container (A) containing a cosmetic agent (a) and
a container (B) containing a cosmetic agent (b),
wherein
the agent (a) in container (A)
(a1) contains one or more sulfinic acid derivatives from the group consisting of
$(H2N)(NH)C(SO_2H)$, formamidinesulfinic acid,
$HN(CH_2SO_2Na)_2$, disodium [(sulfinatomethyl)amino]methanesulfinate
$HN(CH_2SO_2K)_2$, dipotassium [(sulfinatomethyl)amino]methanesulfinate
$HN(CH_2SO_2H)_2$, [(sulfinomethyl)amino]methanesulfinic acid
$N(CH_2SO_2Na)_3$, trisodium [bis(sulfinatomethyl)amino]methanesulfinate
$N(CH_2SO_2K)_3$, tripotassium [bis(sulfinatomethyl)amino]methanesulfinate
$N(CH_2SO_2H)_3$, [bis(sulfinomethyl)amino]methanesulfinic acid
$H_2NCH(CH_3)SO_2Na$, sodium 1-aminoethane-1-sulfinate
$H_2NCH(CH_3)SO_2K$, potassium 1-aminoethane-1-sulfinate
$H_2NCH(CH_3)SO_2H$, 1-aminoethane-1-sulfinic acid
$HN(CH(CH_3)SO_2Na)_2$, disodium 1-[(1-sulfinatoethyl)amino]ethane-1-sulfinate
$HN(CH(CH_3)SO_2K)_2$, dipotassium 1-[(1-sulfinatoethyl)amino]ethane-1-sulfinate
$HN(CH(CH_3)SO_2H)_2$, 1-[(1-sulfinoethyl)amino]ethane-1-sulfinic acid
$N(CH(CH_3)SO_2Na)_3$, trisodium 1-[bis(1-sulfinatoethyl)amino]ethane-1-sulfinate
$N(CH(CH_3)SO_2K)_3$, tripotassium 1-[bis(1-sulfinatoethyl)amino]ethane-1-sulfinate and/or
$N(CH(CH_3)SO_2H)_3$, 1-[bis(1-sulfinoethyl)amino]ethane-1-sulfinic acid,
(a2) contains one or more fatty constituents from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils,
(a3) has a water content of at most 10.0% by weight, based on the total weight of the agent (a),
the agent (b) in container (B)
(b1) has a water content of at least 30.0% by weight, based on the total weight of the agent (b).

The agents (a) and (b) contained in the containers (A) and (B) of the multicomponent packaging unit according to the invention are characterized by an extremely good storage stability even at high temperatures. Furthermore, it has been found in the course of the work leading to this invention that the two agents (a) and (b) can be very conveniently and quickly mixed with one another, and that a very even decoloration result can be achieved with the ready-to-use decoloring agent obtained after the mixing. Moreover, no dust arises during the mixing of the agents (a) and (b). In addition, it has been found that the damage to the hair could be reduced when applying the decoloring agent according to the invention (that is to say when applying the mixture of the agents (a) and (b)). Surprisingly, the decoloration result was also improved in comparison to the agents known from the prior art.

Keratinous fibers, keratin-containing fibers or keratin fibers are to be understood to mean furs, wool, feathers and in particular human hair. Although the agents according to the invention are suitable primarily for lightening and coloring keratin fibers or human hair, in principle nothing stands in the way of a use also in other fields.

The term "colored keratin fibers" is to be understood to mean keratin fibers which have been colored using conventional cosmetic coloring agents known to the person skilled in the art. In particular, "colored keratin fibers" are to be understood to mean fibers which have been colored using the oxidative coloring agents known from the prior art and/or using substantive dyes. In this connection, reference is expressly made to the known monographs, for example Kh. Schrader, Grundlagen und Rezepturen der Kosmetika, 2nd edition, Hüthig Buch Verlag, Heidelberg, 1989, which reflect the relevant knowledge of the person skilled in the art.

The agents (a) and (b) contain the ingredients according to the invention in each case in a cosmetic carrier, which is substantially anhydrous in the case of the agent (a) and contains water in the case of the agent (b).

The agent (a) is presented in substantially anhydrous form and may exist in solid form, as a powder or as a paste. Preferably, the agent (a) is presented in the form of a paste. The agent (a) may also comprise a solvent-containing carrier. Furthermore, the content of fatty constituents from the group (a2) in the agent (a) can also be selected to be so high that the fatty constituents act as a carrier of the agent (a) and therefore, besides the sulfinic acid derivatives (a1), represent the main constituent of the agent (a).

The aqueous cosmetic agent (b) may be for example an agent comprising a suitable aqueous or aqueous-alcoholic carrier. For the purpose of reductive decoloration, such carriers may be for example creams, emulsions, gels or also surfactant-containing foaming solutions, such as for example shampoos, foam aerosols, foam formulations or other preparations suitable for application to the hair. With particular preference, the agents for reductive color removal from keratin fibers are creams, emulsions or flowable gels. The agent (b) is particularly preferably formulated as an emulsion.

Agent (a) in Container (A)

The multicomponent packaging unit (kit-of-parts) according to the invention comprises a first container (A) which contains a cosmetic agent (a). The agent (a) is characterized by its content of one or more sulfinic acid derivatives (a1), which are selected from the group consisting of (H2N)(NH)C(SO2H), formamidinesulfinic acid HN(CH$_2$SO$_2$Na)$_2$, disodium [(sulfinatomethyl)amino] methanesulfinate HN(CH$_2$SO$_2$K)$_2$, dipotassium [(sulfinatomethyl)amino] methanesulfinate HN(CH$_2$SO$_2$H)$_2$, [(sulfinomethyl)amino]methanesulfinic acid N(CH$_2$SO$_2$Na)$_3$, trisodium [bis(sulfinatomethyl)amino] methanesulfinate N(CH$_2$SO$_2$K)$_3$, tripotassium [bis(sulfinatomethyl)amino] methanesulfinate N(CH$_2$SO$_2$H)$_3$, [bis(sulfinomethyl)amino]methane- sulfinic acid H$_2$NCH(CH$_3$)SO$_2$Na, sodium 1-aminoethane-1-sulfinate H$_2$NCH(CH$_3$)SO$_2$K, potassium 1-aminoethane-1-sulfinate H$_2$NCH(CH$_3$)SO$_2$H, 1-aminoethane-1-sulfinic acid HN(CH(CH$_3$)SO$_2$Na)$_2$, disodium 1-[(1-sulfinatoethyl) amino]ethane-1-sulfinate HN(CH(CH$_3$)SO$_2$K)$_2$, dipotassium 1-[(1-sulfinatoethyl) amino]ethane-1-sulfinate HN(CH(CH$_3$)SO$_2$H)$_2$, 1-[(1-sulfinoethyl)amino]ethane- 1-sulfinic acid N(CH(CH$_3$)SO$_2$Na)$_3$, trisodium 1-[bis(1-sulfinatoethyl) amino]ethane-1-sulfinate N(CH(CH$_3$)SO$_2$K)$_3$, tripotassium 1-[bis(1-sulfinatoethyl) amino]ethane-1-sulfinate and/or N(CH(CH$_3$)SO2H)$_3$, 1-[bis(1-sulfinoethyl)amino]ethane- 1-sulfinic acid.

Formamidinesulfinic acid is alternatively also known as thiourea dioxide or as aminoiminomethanesulfinic acid. Formamidinesulfinic acid has the structure of formula (I), but may also be in the form of its tautomers. Formamidinesulfinic acid has the CAS number 1758-73-2 and is commercially available from various suppliers, for example from Sigma Aldrich.

(I)

Disodium [(sulfinatomethyl)amino]methanesulfinate is the disodium salt of [(sulfinomethyl)-amino]methanesulfinic acid and has the structure of formula (II)

(II)

Dipotassium [(sulfinatomethyl)amino]methanesulfinate is the dipotassium salt of [(sulfinomethyl)amino]methanesulfinic acid and has the structure of formula (III)

(III)

[(Sulfinomethyl)amino]methanesulfinic acid has the structure of formula (IV)

(IV)

Trisodium [bis(sulfinatomethyl)amino]methanesulfinate is the trisodium salt of [bis(sulfinomethyl)amino]methanesulfinic acid and has the structure of formula (V)

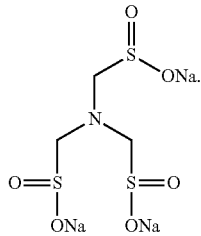
(V)

Tripotassium [bis(sulfinatomethyl)amino]methanesulfinate is the tripotassium salt of [bis(sulfinomethyl)amino]methanesulfinic acid and has the structure of formula (VI)

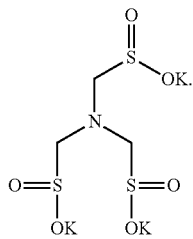
(VI)

[Bis(sulfinomethyl)amino]methanesulfinic acid has the structure of formula (VII)

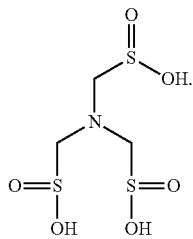
(VII)

Sodium 1-aminoethane-1-sulfinate is the sodium salt of 1-aminoethane-1-sulfinic acid and has the structure of formula (VIII)

(VIII)

Potassium 1-aminoethane-1-sulfinate is the potassium salt of 1-aminoethane-1-sulfinic acid and has the structure of formula (IX)

(IX)

1-Aminoethane-1-sulfinic acid has the structure of formula (X)

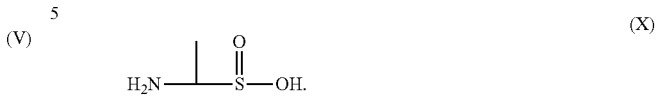
(X)

Disodium 1-[(1-sulfinatoethyl)amino]ethane-1-sulfinate is the disodium salt of 1-[(1-sulfinoethyl)amino]ethane-1-sulfinic acid and has the structure of formula (XI)

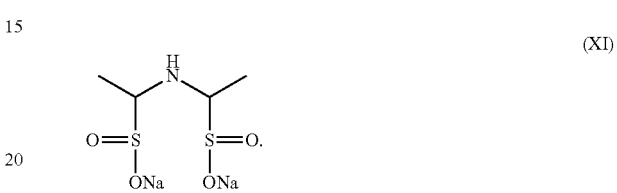
(XI)

Dipotassium 1-[(1-sulfinatoethyl)amino]ethane-1-sulfinate is the dipotassium salt of 1-[(1-sulfinoethyl)amino]ethane-1-sulfinic acid and has the structure of formula (XII)

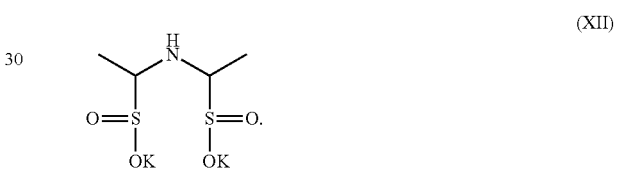
(XII)

1-[(1-Sulfinoethyl)amino]ethane-1-sulfinic acid has the structure of formula (XIII)

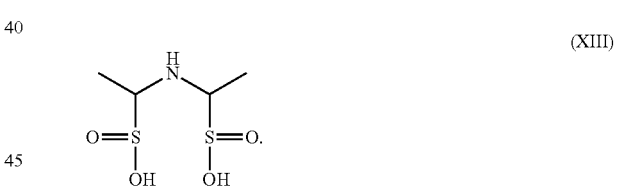
(XIII)

Trisodium 1-[bis(1-sulfinatoethyl)amino]ethane-1-sulfinate is the trisodium salt of 1-[bis(1-sulfinoethyl)amino]ethane-1-sulfinic acid and has the structure of formula (XIV)

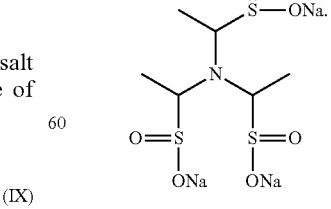
(XIV)

Tripotassium 1-[bis(1-sulfinatoethyl)amino]ethane-1-sulfinate is the tripotassium salt of 1-[bis(1-sulfinoethyl)amino]ethane-1-sulfinic acid and has the structure of formula (XV)

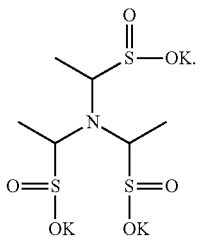

(XV)

1-[Bis(1-sulfinoethyl)amino]ethane-1-sulfinic acid has the structure of formula (XVI)

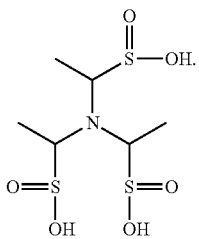

(XVI)

The preparation of the compounds of formulae (II) to (XVI) is described for example in EP 0914516 B1.

The best presentation was formamidinesulfinic acid in paste form since formamidinesulfinic acid was able to be particularly well distributed in finely dispersed form in the fat-containing carrier and in this form had very good storage stability. Moreover, an extremely good decoloration result was obtained when using formamidinesulfinic acid.

During application of the ready-to-use decoloring agent, that is to say after mixing the formamidinesulfinic acid-containing agent (a) with the aqueous carrier (b), the odor emission was also particularly low.

A particularly preferred multicomponent packaging unit (kit-of-parts) is therefore characterized in that the agent (a) in container (A)

(a1) contains (H2N)(NH)C(SO2H) formamidinesulfinic acid as the sulfinic acid derivative.

Furthermore, the sulfinic acid derivative(s) of group (a1) are preferably used in particular quantity ranges. Preferably, the agent (a) presented in substantially anhydrous form contains the sulfinic acid derivative(s) of group (a1) in a total amount of 0.1 to 50.0% by weight, preferably 1.0 to 30.0% by weight, more preferably 1.5 to 20.0% by weight and particularly preferably 2.5 to 10.5% by weight. All stated amounts refer here to the total amount of all sulfinic acid derivatives of group (a1) contained in the agent (a), relative to the total weight of the agent (a).

Particular preference is therefore given to a multicomponent packaging unit (kit-of-parts) which is characterized in that the agent (a) in container (A) contains, based on the total weight of the agent (a), one or more sulfinic acid derivatives from the group (a1) in a total amount of 0.1 to 50.0% by weight, preferably 1.0 to 30.0% by weight, more preferably 1.5 to 20.0% by weight and particularly preferably 2.5 to 10.5% by weight.

Very particular preference is given to a multicomponent packaging unit (kit-of-parts) for reductive decoloration of colored keratin fibers which is characterized in that the agent (a) in container (A)

(a1) contains 0.1 to 50.0% by weight formamidinesulfinic acid (alternative name thiourea dioxide).

Very particular preference is given to a multicomponent packaging unit (kit-of-parts) for reductive decoloration of colored keratin fibers which is characterized in that the agent (a) in container (A)

(a1) contains 1.0 to 30.0% by weight formamidinesulfinic acid (alternative name thiourea dioxide).

Very particular preference is given to a multicomponent packaging unit (kit-of-parts) for reductive decoloration of colored keratin fibers which is characterized in that the agent (a) in container (A)

(a1) contains 1.5 to 20.0% by weight formamidinesulfinic acid (alternative name thiourea dioxide).

Very particular preference is given to a multicomponent packaging unit (kit-of-parts) for reductive decoloration of colored keratin fibers which is characterized in that the agent (a) in container (A)

(a1) contains 2.5 to 10.5% by weight formamidinesulfinic acid (alternative name thiourea dioxide).

In principle, the agent (a) may also contain further reducing agents besides the sulfinic acid derivatives of group (a1). However, it has been found that some reducing agents are incompatible with the sulfinic acid derivatives of group (a1), adversely affect the storage stability or lead to a surprisingly high amount of damage to the hair. Sulfites in particular, such as for example sodium sulfite ($Na_2SO_3$), potassium sulfite ($K_2SO_3$), ammonium sulfite (($NH_4)_2SO_3$) or also bisulfites, have proven to be of little advantage when used in combination with the sulfinic acid derivatives of formula (a1) since the hair felt brittle and straw-like after decoloration when using these combinations.

For this reason, preference is given to a multicomponent packaging unit (kit-of-parts) for reductive decoloration of colored keratin fibers which is characterized in that the agent (a) in container (A) contains, based on the total weight of the agent (a), ($a^\#$) sulfites in a total amount of less than 1.0% by weight, preferably less than 0.5% by weight, more preferably less than 0.1% by weight.

In other words, preference is given to a multicomponent packaging unit (kit-of-parts) for reductive decoloration of colored keratin fibers which is characterized in that the agent (a) in container (A) contains, based on the total weight of the agent (a), ($a^\#$) sulfites from the group consisting of sodium sulfite ($Na_2SO_3$), potassium sulfite ($K_2SO_3$) and ammonium sulfite (($NH_4)_2SO_3$) in a total amount of less than 1.0% by weight, preferably less than 0.5% by weight, more preferably less than 0.1% by weight.

As a second ingredient (a2) which is essential to the invention, the agent (a) contains at least one or more fatty constituents from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils.

In the context of the invention, "fatty constituents" will be understood to mean organic compounds having a solubility in water at room temperature (22° C.) and atmospheric pressure (760 mmHg) of less than 1% by weight, preferably less than 0.1% by weight.

The definition of the fatty constituents explicitly encompasses only uncharged (that is to say nonionic) compounds. Fatty constituents have at least one saturated or unsaturated alkyl group having at least 12 C atoms. The molecular weight of the fatty constituents is at most 5000 g/mol, preferably at most 2500 g/mol and particularly preferably at most 1000 g/mol. The fatty constituents are neither polyoxyalkylated nor polyglycerylated compounds. In this connection, polyalkoxylated compounds are those compounds during the preparation of which at least 2 alkylene oxide units have been reacted. Analogously, polyglycerylated compounds are those compounds during the preparation of which at least two glycerol units have been reacted.

Since, in the context of the present invention, explicitly only nonionic substances are regarded as fatty constituents, charged compounds, such as for example fatty acids and the salts of fatty acids, do not fall under the group of fatty constituents.

Preferred fatty constituents are the constituents selected from the group consisting of $C_{12}$-$C_{30}$ fatty alcohols, $C_{12}$-$C_{30}$ fatty acid triglycerides, $C_{12}$-$C_{30}$ fatty acid-monoglycerides, $C_{12}$-$C_{30}$ fatty acid diglycerides, $C_{12}$-$C_{30}$ fatty acid esters and hydrocarbons.

The $C_{12}$-$C_{30}$ fatty alcohols may be saturated, mono- or polyunsaturated, linear or branched fatty alcohols having 12 to 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachidyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonyl alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives of branched fatty alcohols are 2-octyldodecanol, 2-hexyldodecanol and/or 2-butyldodecanol.

In the context of the present invention, a $C_{12}$-$C_{30}$ fatty acid triglyceride will be understood to mean the triesters of the trivalent alcohol glycerol with three fatty acid equivalents. In this regard, both structurally identical and also different fatty acids may be involved in ester formations within a triglyceride molecule.

According to the invention, fatty acids will be understood to mean saturated or unsaturated, unbranched or branched, unsubstituted or substituted $C_{12}$-$C_{30}$ carboxylic acids. Unsaturated fatty acids may be mono- or polyunsaturated. In the case of an unsaturated fatty acid, the C—C double bond(s) thereof may have the cis or trans configuration.

Particularly suitable are the fatty acid triglycerides in which at least one of the ester groups is formed originating from glycerol with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid] and/or nervonic acid [(15Z)-tetracos-15-enoic acid].

The fatty acid triglycerides may also be of natural origin. The fatty acid triglycerides occurring in soybean oil, peanut oil, olive oil, sunflower oil, macadamia nut oil, Moringa oil, apricot kernel oil, Marula oil and/or optionally hydrogenated castor oil, and mixtures thereof, are particularly suitable for use in the agent (a).

A $C_{12}$-$C_{30}$ fatty acid monoglyceride will be understood to mean the monoester of the trivalent alcohol glycerol with one fatty acid equivalent. In this case, either the middle hydroxyl group of the glycerol or the terminal hydroxyl group of the glycerol can be esterified with the fatty acid.

Particularly suitable are the $C_{12}$-$C_{30}$ fatty acid monoglycerides in which one hydroxyl group of the glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid] or nervonic acid [(15Z)-tetracos-15-enoic acid].

A $C_{12}$-$C_{30}$ fatty acid diglyceride will be understood to mean the diester of the trivalent alcohol glycerol with two fatty acid equivalents. In this case, either the middle and one terminal hydroxyl group of the glycerol can be esterified with two fatty acid equivalents, or else both terminal hydroxyl groups of the glycerol are esterified with in each case one fatty acid. The glycerol may in this case be esterified either with two structurally identical or with two different fatty acids.

Particularly suitable are the fatty acid diglycerides in which at least one of the ester groups is formed originating from glycerol with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid] and/or nervonic acid [(15Z)-tetracos-15-enoic acid].

In the context of the present invention, a $C_{12}$-$C_{30}$ fatty acid ester will be understood to mean the monoester of a fatty acid and an aliphatic, monovalent alcohol, the alcohol comprising up to 6 C atoms. As suitable alcohols, mention may be made for example of ethanol, n-propanol, isopropanol, 1-butanol, isobutanol, tert-butanol, n-pentanol, isopentanol or n-hexanol. Preferred alcohols are ethanol and isopropanol.

Preferred $C_{12}$-$C_{30}$ fatty acid esters are the esters formed in the esterification of the alcohols ethanol and/or propanol with one of the fatty acids from the group consisting of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid] and/or nervonic acid [(15Z)-tetracos-15-enoic acid]. Among the fatty acid esters, very particular preference is given to isopropyl myristate.

Hydrocarbons are compounds which consist exclusively of carbon and hydrogen atoms and which have 8 to 250 C atoms, preferably 8 to 150 C atoms. In this connection, particular preference is given to aliphatic hydrocarbons such as for example mineral oils, liquid paraffin oils (for example liquid paraffin or light liquid paraffin), isoparaffin oils, semisolid paraffin oils, paraffin waxes, hard paraffin (solid paraffin), Vaseline and polydecenes.

Liquid paraffin oils (liquid paraffin and light liquid paraffin) have proven to be particularly suitable in this regard. With very particular preference, the hydrocarbon is liquid paraffin, also called white oil. Liquid paraffin is a mixture of purified, saturated, aliphatic hydrocarbons, which consists for the most part of hydrocarbon chains with a C-chain distribution of 25 to 35 C atoms.

In the context of the invention, silicone oils will be understood to mean hydrophobic compounds which contain at least one Si atom, preferably a plurality of Si atoms, have a molecular weight of at most 5000 g/mol and are liquid at room temperature (22° C.) and atmospheric pressure (760 mmHg), that is to say the melting point of silicone oils is (at atmospheric pressure) below 22° C.

A particularly preferred multicomponent packaging unit (kit-of-parts) for reductive decoloration of colored keratin fibers is characterized in that
the agent (a) in container (A)
(a2) contains one or more fatty constituents from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters and/or hydrocarbons.

Preference is also given to a multicomponent packaging unit (kit-of-parts) for reductive decoloration of colored keratin fibers which is characterized in that
the agent (a) in container (A)
(a2) contains one or more fatty constituents from the group formed of dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachidyl alcohol (eicosan-1-ol), heneicosyl alcohol (heneicosan-1-ol) and/or behenyl alcohol (docosan-1-ol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonyl alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol), 2-octyldodecanol, 2-hexyldodecanol and/or 2-butyldodecanol.

Preference is also given to a multicomponent packaging unit (kit-of-parts) for reductive decoloration of colored keratin fibers which is characterized in that
the agent (a) in container (A)
(a2) contains one or more fatty constituents from the group of fatty acid triglycerides in which at least one of the ester groups is formed originating from glycerol with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid] and/or nervonic acid [(15Z)-tetracos-15-enoic acid].

Preference is also given to a multicomponent packaging unit (kit-of-parts) for reductive decoloration of colored keratin fibers which is characterized in that
the agent (a) in container (A)
(a2) contains one or more fatty constituents from the group of hydrocarbons which is formed by mineral oils, liquid paraffin oils, isoparaffin oils, semisolid paraffin oils, paraffin waxes and/or hard paraffin (solid paraffin), Vaseline and polydecenes.

The total content of fatty constituents (a2) in the agent (a) has proven to be an essential parameter in reducing the dust production. A reduction in dust production occurs even when small amounts of fatty constituents are used. However, in order to be able to ensure the best possible dust control, it has proven to be optimal to use the fatty constituents (a2) in a total amount of at least 10% by weight. For this reason, it is particularly preferred if the agent (a) contains the fatty constituents (a2) in a total amount of 10.0 to 90.0% by weight, preferably 20.0 to 86.0% by weight, more preferably 25.0 to 84.0% by weight and particularly preferably 30.0 to 80.0% by weight. When the fatty constituents (a2) were used in the specified preferred and particularly preferred total amounts in the agent (a), the reducing agent could moreover be effectively protected against the effects of atmospheric oxygen and in this way the storage stability could be significantly improved.

Very particular preference is therefore explicitly given to a multicomponent packaging unit (kit-of-parts) for reductive decoloration of colored keratin fibers which is characterized in that
the agent (a) in container (A) contains, based on the total weight of the agent (a), one or more fatty constituents of the group (a2) in a total amount of 10.0 to 90.0% by weight, preferably 20.0 to 86.0% by weight, more preferably 25.0 to 84.0% by weight and particularly preferably 30.0 to 80.0% by weight.

For reducing the dust formation and making the reducing agent inert with respect to oxygen in the air, the use of hydrocarbons has proven to be very particularly effective. In particular, paraffin oils and paraffin waxes are particularly capable of encasing the sulfinic acid derivatives of group (a1) in a paste-like manner and thus transforming the latter into a very stable paste form. For this reason, very particular preference is explicitly given to using as the reducing agent (a2) one or more hydrocarbons in a total amount of 15.0 to 90.0% by weight, preferably 20.0 to 85.0% by weight, more preferably 25.0 to 80.0% by weight and particularly preferably 30.0 to 75.0% by weight. All stated amounts by weight again refer to the total weight of all hydrocarbons contained in the agent (a), relative to the total weight of the agent (a).

A multicomponent packaging unit (kit-of-parts) to which very particular preference is explicitly given is therefore characterized in that the agent (a) in container (A)

(a2) contains one or more hydrocarbons in a total amount of 15.0 to 90.0% by weight, preferably 20.0 to 85.0% by weight, more preferably 25.0 to 80.0% by weight and particularly preferably 30.0 to 75.0% by weight, based on the total weight of the agent (a).

In a manner essential to the invention, the agent (a) is also characterized in that it (a3) is presented in substantially anhydrous form. The term "substantially anhydrous" will be understood here to mean that the water content of the agent (a) is at most 10.0% by weight. Preferably, however, the water content of the agent (a) is less than 10.0% by weight and is preferably at most 8.0% by weight, more preferably at most 5.0% by weight, even more preferably at most 3.0% by weight and very particularly preferably at most 1.0% by weight. Here, all the stated percentages by weight are based on the total weight of the agent (a).

A low water content may be desired in the agent (a) in order to integrate in the agent, besides the sulfinic acid derivatives (a1) and the fatty constituents (a2), also various hydrophilic ingredients (for example perfumes or hydrophilic care substances). These hydrophilic ingredients may for example first be pre-dissolved in water and then emulsified or dispersed in the fatty constituents (a2) with the aid of surfactants. In this case, the fatty constituents (a2) at the same time also act as a carrier, and a W/O emulsion is formed.

Additional ingredients or active substances which contain up to a certain percentage of water may also be used in the agent (a). In this connection, it has been found that a water content of up to 10% by weight does not greatly impair the storage stability of the agent (a).

However, in order to achieve an optimal storage stability even at high temperatures, it has proven to be advantageous if the water content of the agent (a) is at most 8.0% by weight, preferably at most 5.0% by weight, more preferably at most 3.0% by weight and particularly preferably at most 1.0% by weight, based on the total weight of the agent (a).

Another very particularly preferred multicomponent packaging unit (kit-of-parts) for reductive decoloration of colored keratin fibers is therefore characterized in that the agent (a) in container (A)

(a3) has a water content of at most 8.0% by weight, preferably at most 5.0% by weight, more preferably at most 3.0% by weight and particularly preferably at most 1.0% by weight, based on the total weight of the agent (a).

The agent (a) may additionally also contain further ingredients and/or active substances. In particular, the use of nonionic surfactants (a4) in the agent (a) has proven to be particularly advantageous. It has been found that nonionic surfactants have a very good compatibility both with the sulfinic acid derivatives (a1) and also in particular with the fatty constituents (a2), so that the agent (a) can be prepared in an easy and reproducible manner and does not separate during storage. By using one or more nonionic surfactants, it was also possible to achieve an optimal miscibility with the agent (b).

The nonionic surfactant(s) may be used for example in total amounts of 0.1 to 15.0% by weight, preferably 0.5 to 12.5% by weight, more preferably 1.0 to 10.0% by weight and particularly preferably 1.5 to 8.0% by weight, based on the total weight of the agent (a).

Preference is therefore also given to a multicomponent packaging unit (kit-of-parts) for reductive decoloration of colored keratin fibers which is characterized in that the agent (a) in container (A) additionally (a4) contains one or more nonionic surfactants in a total amount of 0.1 to 15.0% by weight, preferably 0.5 to 12.5% by weight, more preferably 1.0 to 10.0% by weight and particularly preferably 1.5 to 8.0% by weight, based on the total weight of the agent (a).

Surfactants will be understood to mean amphiphilic (bi-functional) compounds having at least one hydrophobic residue and at least one hydrophilic moiety. The hydrophobic moiety is usually a hydrocarbon chain having 10 to 30 carbon atoms. In the case of the nonionic surfactants, the hydrophilic moiety comprises an uncharged, strongly polar structural unit.

Nonionic surfactants contain as the hydrophilic group, for example, a polyol group, a polyalkylene glycol ether group or a combination of a polyol group and a polyglycol ether group. Such compounds are for example addition products of 2 to 50 mol ethylene oxide and/or 2 to 50 mol propylene oxide onto linear and branched fatty alcohols having 12 to 30 C atoms, the fatty alcohol polyglycol ethers or fatty alcohol polypropylene glycol ethers or mixed fatty alcohol polyethers, addition products of 2 to 50 mol ethylene oxide and/or 2 to 50 mol propylene oxide onto linear and branched fatty acids having 6 to 30 C atoms, the fatty acid polyglycol ethers or fatty acid polypropylene glycol ethers or mixed fatty acid polyethers, addition products of 2 to 50 mol ethylene oxide and/or 2 to 50 mol propylene oxide onto linear and branched alkylphenols having 8 to 15 C atoms in the alkyl group, the alkylphenol polyglycol ethers or alkylphenol polypropylene glycol ethers or mixed alkylphenol polyethers, addition products of 2 to 50 mol ethylene oxide and/or 2 to 50 mol propylene oxide, closed at an end group by a methyl or $C_2$-$C_6$ alkyl radical, onto linear and branched fatty alcohols having 8 to 30 C atoms, onto fatty acids having 8 to 30 C atoms and onto alkylphenols having 8 to 15 C atoms in the alkyl group, such as for example the types available under the trade names Dehydol® LS, Dehydol® LT (Cognis), $C_{12}$-$C_{30}$ fatty acid mono- and diesters of addition products of 2 to 30 mol ethylene oxide onto glycerol, addition products of 5 to 60 mol ethylene oxide onto castor oil and hydrogenated castor oil, polyol fatty acid esters, such as for example the commercial product Hydagen® HSP (Cognis) or Sovermol® types (Cognis), polyalkoxylated triglycerides, polyalkoxylated fatty acid alkyl esters of formula (Tnio-1)

$$R^1CO\text{---}(OCH_2CHR^2)_wOR^3 \qquad \text{(Tnio-1)}$$

in which $R^1CO$ represents a linear or branched, saturated and/or unsaturated acyl radical having 6 to 22 carbon atoms, $R^2$ represents hydrogen or methyl, $R^3$ represents linear or branched alkyl radicals having 1 to 4 carbon atoms, and w represents numbers from 2 to 20, amine oxides, hydroxy mixed ethers, such as for example those described in DE OS19738866, sorbitan fatty acid esters and addition products of ethylene oxide onto sorbitan fatty acid esters, such as for example the polysorbates, sugar fatty acid esters and addition products of ethylene oxide onto sugar fatty acid esters, addition products of ethylene oxide onto fatty acid alkanolamides and fatty amines, sugar surfactants of the alkyl- and alkenyloligoglycoside type, or sugar surfactants of the fatty acid N-alkylpolyhydroxyalkylamide type.

$C_{12}$-$C_{30}$ fatty alcohols, $C_{12}$-$C_{30}$ fatty acid triglycerides, $C_{12}$-$C_{30}$ fatty acid-monoglycerides, $C_{12}$-$C_{30}$ fatty acid diglycerides and $C_{12}$-$C_{30}$ fatty acid esters have no strongly polar end group (as is also clear from the low HLB values of the compounds of this group). In the context of this invention, they are regarded as fatty constituents and therefore are not nonionic surfactants according to the definition of the present invention.

Furthermore, the agent (a) may additionally also contain one or more nonionic polymers (a5). The nonionic polymer(s) may be used for example in total amounts of 0.1 to 15.0% by weight, preferably 0.2 to 10.5% by weight, more preferably 0.25 to 7.5% by weight and particularly preferably 0.3 to 5.0% by weight, based on the total weight of the agent (a).

Another particularly preferred multicomponent packaging unit (kit-of-parts) for reductive decoloration of colored keratin fibers is characterized in that the agent (a) in container (A) additionally (a5) contains one or more nonionic polymers in a total amount of 0.1 to 15.0% by weight, preferably 0.2 to 10.5% by weight, more preferably 0.25 to 7.5% by weight and particularly preferably 0.3 to 5.0% by weight, based on the total weight of the agent (a).

Polymers will be understood to mean macromolecules which have a molecular weight of at least 1000 g/mol, preferably at least 2500 g/mol, particularly preferably at least 5000 g/mol, and which consist of identical repeating organic units. Polymers are produced by polymerization of one monomer type or by polymerization of various monomer types which are structurally different from one another. If the polymer is produced by polymerization of one monomer type, it is referred to as a homopolymer. If structurally different monomer types are used in the polymerization, the resulting polymer is referred to as a copolymer.

The maximum molecular weight of the polymer depends on the degree of polymerization (number of polymerized monomers) and is determined by the polymerization method. In the context of the present invention, it is preferred if the maximum molecular weight of the zwitterionic polymer (d) is not more than $10^7$ g/mol, preferably not more than $10^6$ g/mol and particularly preferably not more than $10^5$ g/mol.

Nonionic polymers are characterized in that they have no charges, that is to say nonionic polymers in the context of the present invention are produced by homopolymerization or copolymerization of uncharged monomers.

Examples of suitable nonionic polymers are vinylpyrrolidinone/vinyl acrylate copolymers, polyvinylpyrrolidinone, vinylpyrrolidinone/vinyl acetate copolymers, polyethylene glycols, ethylene/propylene/styrene copolymers and/or butylene/ethylene/styrene copolymers.

Agent (b) in Container (B)

The multicomponent packaging unit according to the invention comprises a second container (B) which contains an agent (b). This agent (b) is a cosmetic carrier formulation which has a water content of at least 30.0% by weight, based on the total weight of the agent (b).

In one preferred embodiment, the agent (b) is presented in such a way that the water content thereof is at least 40.0% by weight, preferably at least 50.0% by weight, more preferably at least 55.0% by weight and very particularly preferably at least 60.0% by weight, based on the total weight of the agent (b).

Preference is thus also given to a multicomponent packaging unit (kit-of-parts) for reductive decoloration of colored keratin fibers which is characterized in that the agent (b) in container (B)

(b1) has a water content of at least 40.0% by weight, preferably at least 50.0% by weight, more preferably at least 55.0% by weight and very particularly preferably at least 60.0% by weight, based on the total weight of the agent (b).

In the course of the work leading to this invention, it has been found that the pH of the ready-to-use decoloring agent is preferably made alkaline in order to achieve an optimal decoloring effect. The sulfinic acid derivatives of group (a1) exhibited the best effect at a pH of 7.0 to 13.0. It has also proven to be particularly advantageous if the alkalizing agent necessary for adjusting the pH is present in the aqueous agent (b). In this way, it can reliably be ensured that contact between sulfinic acid derivatives (a1) and alkalizing agent takes place just prior to application after mixing the agents (a) and (b).

In principle, the alkaline pH may be set using various alkalizing agents. Suitable alkalizing agents are for example sodium hydroxide, potassium hydroxide, sodium carbonate, sodium hydrogen carbonate, potassium carbonate or potassium hydrogen carbonate. In this connection, however, it has been found that the reductively decoloring sulfinic acid derivatives (a1) were best able to diffuse into the hair fibers when nitrogen-containing compounds such as ammonia, alkanolamines and/or basic amino acids were used as the alkalizing agent.

Preference is thus also given to a multicomponent packaging unit (kit-of-parts) for reductive decoloration of colored keratin fibers which is characterized in that the agent (b) in container (B)

(b2) contains one or more alkalizing agents from the group consisting of ammonia, alkanolamines and/or basic amino acids.

The pH values of the present invention were measured using a glass electrode of type N 61 from the company Schott, at a temperature of 22° C.

The alkanolamines which can be used in the agent (b) according to the invention are preferably selected from primary amines having a $C_2$-$C_6$ alkyl parent substance which carries at least one hydroxyl group. Preferred alkanolamines are selected from the group formed of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol.

Alkanolamines which are particularly preferred according to the invention are selected from 2-aminoethan-1-ol and/or 2-amino-2-methylpropan-1-ol. A particularly preferred embodiment is therefore characterized in that the agent (b) according to the invention contains as the alkalizing agent an alkanolamine selected from 2-aminoethan-1-ol and/or 2-amino-2-methylpropan-1-ol.

In the context of the invention, an amino acid is an organic compound which contains in its structure at least one protonizable amino group and at least one —COOH or —SO$_3$H group. Preferred amino acids are aminocarboxylic acids, in particular α-(alpha)-aminocarboxylic acids and ω-aminocarboxylic acids, particular preference being given to α-aminocarboxylic acids.

According to the invention, basic amino acids are understood to mean those amino acids which have an isoelectric point pI of greater than 7.0.

Basic α-aminocarboxylic acids contain at least one asymmetric carbon atom. In the context of the present invention, both possible enantiomers can be used equally as a specific compound or mixtures thereof, in particular as racemates. However, it is particularly advantageous to use the naturally preferentially occurring isomer forms, usually in L-configuration.

The basic amino acids are preferably selected from the group formed of arginine, lysine, ornithine and histidine, particularly preferably arginine and lysine. In another particularly preferred embodiment, therefore, an agent according to the invention is characterized in that the alkalizing agent is a basic amino acid from the group consisting of arginine, lysine, ornithine and/or histidine.

Preference is thus also given to a multicomponent packaging unit (kit-of-parts) for reductive decoloration of colored keratin fibers which is characterized in that
the agent (b) in container (B)
(b2) contains one or more alkalizing agents from the group consisting of ammonia, 2-aminoethan-1-ol (monoethanolamine), 3-aminopropan-1-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine and/or histidine.

Preferred agents (b) according to the invention may also contain alkalizing agent mixtures such as for example a mixture of different alkanolamines, a mixture of basic amino acids and/or a mixture of alkanolamines and basic amino acids. With particular preference, the alkalizing agents are used in particular combinations: 2-aminoethan-1-ol/2-amino-2-methylpropan-1-ol; 2-aminoethan-1-ol/arginine; 2-aminoethan-1-ol/lysine; 2-aminoethan-1-ol/ornithine; 2-aminoethan-1-ol/histidine; 2-amino-2-methylpropan-1-ol/arginine; 2-amino-2-methylpropan-1-ol/lysine; 2-amino-2-methylpropan-1-ol/ornithine; 2-amino-2-methylpropan-1-ol/histidine; arginine/lysine; arginine/ornithine; arginine/histidine; lysine/ornithine; lysine/histidine and/or ornithine/histidine.

In addition, the agent may contain further alkalizing agents, in particular inorganic alkalizing agents. Inorganic alkalizing agents which can be used according to the invention are preferably selected from the group formed of sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Although the preferred pH of the agent (b) lies in the alkaline range, in order to finely set the desired pH the agents (b) could also contain small amounts of acidifying agents in addition to the alkalizing agent. Acidifying agents which are preferred according to the invention are edible acids, such as for example citric acid, acetic acid, malic acid or tartaric acid, as well as dilute mineral acids.

One or more acids from the group consisting of citric acid, tartaric acid, malic acid, lactic acid, acetic acid, sulfuric acid, hydrochloric acid, phosphoric acid, methanesulfonic acid, benzoic acid, malonic acid, oxalic acid and/or 1-hydroxyethane-1,1-diphosphonic acid have proven to be suitable for finely setting the desired pH. Preferably, the acid(s) will be selected from the group consisting of citric acid, tartaric acid, malic acid, lactic acid, methanesulfonic acid, oxalic acid, malonic acid, benzoic acid, hydrochloric acid, sulfuric acid, phosphoric acid and/or 1-hydroxyethane-1,1-diphosphonic acid.

The pH of the aqueous agent (b) is preferably set to a value of 7.5 to 12.5, preferably 8.0 to 12.0, more preferably 8.5 to 11.5 and particularly preferably 9.0 to 11.0.

Particular preference is also given to a multicomponent packaging unit (kit-of-parts) which is characterized in that the agent (b) in container (B)
(b3) has a pH of 7.5 to 12.5, preferably 8.0 to 12.0, more preferably 8.5 to 11.5 and particularly preferably 9.0 to 11.0.

The agent (b) is provided as a liquid preparation, to which further surface-active substances may be added. These are preferably selected from anionic, zwitterionic, amphoteric and nonionic surfactants.

As anionic surfactants, the agent (b) may contain for example fatty acids, alkyl sulfates, alkyl ether sulfates and ether carboxylic acids having 10 to 20 C atoms in the alkyl group and up to 16 glycol ether groups in the molecule.

The agent (b) may also contain one or more zwitterionic surfactants, such as for example betaines, N-alkyl-N,N-dimethylammonium glycinates, N-acylaminopropyl-N,N-dimethylammonium glycinates and 2-alkyl-3-carboxymethyl-3-hydroxy-ethylimidazolines.

Agents (b) which are suitable according to the invention are also characterized in that the agent (b) additionally contains at least one amphoteric surfactant. Preferred amphoteric surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids. Particularly preferred amphoteric surfactants are N-cocoalkylaminopropionate, cocoacylaminoethylaminopropionate and $C_{12}$-$C_{18}$ acyl sarcosine.

It has proven to be particularly advantageous if the agent (b) additionally contains nonionic surfactants (b4). Preferred nonionic surfactants are
alkyl polyglycosides
alkylene oxide addition products onto fatty alcohols and fatty acids with in each case 10 to 60 mol ethylene oxide per mole of fatty alcohol or fatty acid, and
fatty acid triglycerides which are ethoxylated with 10 to 60 ethylene oxide units.

Particular preference is thus also given to a multicomponent packaging unit (kit-of-parts) which is characterized in that the agent (b) in container (B) additionally contains one or more nonionic surfactants from the group consisting of
$C_{12}$-$C_{30}$ fatty alcohols which are ethoxylated with 10 to 60 ethylene oxide units and/or
fatty acid triglycerides which are ethoxylated with 10 to 60 ethylene oxide units.

The nonionic, zwitterionic, amphoteric and/or anionic surfactants may be used in amounts of 0.1 to 25.0% by weight, preferably 0.3 to 15.0% by weight and very particularly preferably 0.5 to 5.0% by weight, based on the total weight of the agent (b).

In the optimally presented ready-to-use decoloring agent, the viscosity is set so that the agent on the one hand is thin enough to ensure sufficient diffusion of all active substances from the agent into the hair fibers but on the other hand is also thick enough to avoid any dripping during application. For this reason, the ready-to-use decoloring agents preferably contain a thickener. With particular preference, the thickener is incorporated in the aqueous agent (b).

According to another preferred embodiment, the thickening agent is an anionic synthetic polymer. Preferred anionic groups are the carboxylate group and sulfonate group.

Examples of anionic monomers of which the polymeric anionic thickening agents may consist are acrylic acid, methacrylic acid, crotonic acid, itaconic acid, maleic anhydride and 2-acrylamido-2-methylpropanesulfonic acid. In this connection, some or all of the acidic groups may be in the form of the sodium, potassium, ammonium, mono- or triethanolammonium salt. Preferred monomers are maleic anhydride and, in particular, 2-acrylamido-2-methylpropanesulfonic acid and acrylic acid.

Preferred anionic homopolymers are uncrosslinked and crosslinked polyacrylic acids. In this connection, allyl ethers of pentaerythritol, of sucrose and of propylene may be preferred crosslinking agents. Such compounds are commercially available for example under the trade name Carbopol®. Preference is also given to the homopolymer of 2-acrylamido-2-methylpropanesulfonic acid, which is commercially available for example under the name Rheothik® 11-80.

Within this first embodiment, it may also be preferred to use copolymers of at least one anionic monomer and at least one nonionogenic monomer. With regard to the anionic monomers, reference is made to the substances listed above. Preferred nonionogenic monomers are acrylamide, methacrylamide, acrylic esters, methacrylic esters, itaconic mono- and diesters, vinylpyrrolidinone, vinyl ether and vinyl ester.

Preferred anionic copolymers are for example copolymers of acrylic acid, methacrylic acid or $C_1$-$C_6$ alkyl esters thereof, such as those sold under the INCI name Acrylates Copolymer. A preferred commercial product is for example Aculyn® 33 from the company Rohm & Haas. However, preference is also given to copolymers of acrylic acid, methacrylic acid or $C_1$-$C_6$ alkyl esters thereof and the esters of an ethylenically unsaturated acid and an alkoxylated fatty alcohol. Suitable ethylenically unsaturated acids are in particular acrylic acid, methacrylic acid and itaconic acid; suitable alkoxylated fatty alcohols are in particular Steareth-20 or Ceteth-20. Such copolymers are sold by the company Rohm & Haas under the trade name Aculyn® 22 and by the company National Starch under the trade names Structure® 2001 and Structure® 3001.

Preferred anionic copolymers are also acrylic acid/acrylamide copolymers and in particular polyacrylamide copolymers with sulfonic acid group-containing monomers. A particularly preferred anionic copolymer consists of 70 to 55 mol % acrylamide and 30 to 45 mol % 2-acrylamido-2-methylpropanesulfonic acid, wherein some or all of the sulfonic acid groups are in the form of the sodium, potassium, ammonium, mono- or triethanolammonium salt. This copolymer can also be in crosslinked form, wherein as the crosslinking agents use is preferably made of polyolefinically unsaturated compounds such as tetraallyloxythane, allylsucrose, allylpentaerythritol and methylenebisacrylamide. Such a polymer is contained in the commercial products Sepigel® 305 and Simulgel® 600 from the company SEPPIC. The use of these compounds, which in addition to the polymer component also contain a hydrocarbon mixture ($C_{13}$-$C_{14}$ isoparaffin or isohexadecane) and a nonionogenic emulsifier (Laureth-7 or Polysorbate-80), has proven to be particularly advantageous in the context of the teaching according to the invention.

Polymers of maleic anhydride and methyl vinyl ether, in particular those with crosslinkages, are also preferred thickening agents. A maleic acid/methyl vinyl ether copolymer crosslinked with 1,9-decadiene is commercially available under the name Stabileze® QM.

Preferably, the agent according to the invention may additionally contain at least one anionic acrylic acid and/or methacrylic acid polymer or copolymer. Preferred polymers of this type are:
  polymers consisting for example of at least 10% by weight acrylic acid low alkyl ester, 25 to 70% by weight methacrylic acid and optionally up to 40% by weight of a further comonomer,
  mixed polymers consisting of 50 to 75% by weight ethyl acrylate, 25 to 35% by weight acrylic acid and 0 to 25% by weight other comonomers. Suitable dispersions of this type are commercially available, for example under the trade name Latekoll® D (BASF),
  copolymers of 50 to 60% by weight ethyl acrylate, 30 to 40% by weight methacrylic acid and 5 to 15% by weight acrylic acid, crosslinked with ethylene glycol dimethacrylate.

According to another embodiment, the thickening agent is a cationic synthetic polymer. Preferred cationic groups are quaternary ammonium groups. In particular, those polymers in which the quaternary ammonium groups are bonded via a $C_1$-$C_4$ hydrocarbon group to a polymer main chain constructed of acrylic acid, methacrylic acid or derivatives thereof have proven to be particularly suitable.

Homopolymers of general formula (HP-1),

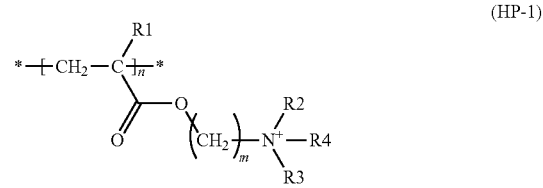

(HP-1)

in which R1=—H or —$CH_3$, R2, R3 and R4 independently of one another are selected from $C_1$-$C_4$ alkyl, alkenyl or hydroxyalkyl groups, m=1, 2, 3 or 4, n is a natural number and $X^-$ is a physiologically acceptable organic or inorganic anion, and copolymers consisting substantially of the monomer units listed in formula (HP-1) and nonionogenic monomer units, are particularly preferred cationic polymeric gel formers. Within the framework of these polymers, preference is given according to the invention to those for which at least one of the following conditions applies:
  R1 represents a methyl group
  R2, R3 und R4 represent methyl groups
  m has the value 2.

Suitable physiologically acceptable counter-ions $X^-$ are for example halide ions, sulfate ions, phosphate ions, methosulfate ions and organic ions such as lactate, citrate, tartrate and acetate ions. Preference is given to halide ions, in particular chloride.

A particularly suitable homopolymer is the, if desired crosslinked, poly(methacryloyloxyethyltrimethylammonium chloride) with the INCI name Polyquarternium-37. The crosslinking may take place, if desired, using polyolefinically unsaturated compounds, for example divinylbenzene, tetraallyloxyethane, methylenebisacrylamide, diallyl ether, polyallyl polyglyceryl ether, or allyl ethers of sugars or sugar derivatives, such as erythritol, pentaerythritol, arabitol, mannitol, sorbitol, sucrose or glucose. Methylenebisacrylamide is a preferred crosslinking agent.

The homopolymer is preferably used in the form of a nonaqueous polymer dispersion which should have a polymer content of not less than 30% by weight. Such polymer dispersions are commercially available under the names Salcare® SC 95 (approximately 50% polymer content, other component: mineral oil (INCI name: Mineral Oil) and tridecylpolyoxypropylene polyoxyethylene ether (INCI name: PPG-1-Trideceth-6)) and Salcare® SC 96 (approximately 50% polymer content, other components: mixture of diesters of propylene glycol with a mixture of caprylic and capric acid (INCI name: propylene glycol dicaprylate/dicaprate) and tridecylpolyoxypropylene polyoxyethylene ether (INCI name: PPG-1-Trideceth-6)).

Copolymers with monomer units according to formula (HP-1) contain, as nonionogenic monomer units, preferably acrylamide, methacrylamide, acrylic $C_1$-$C_4$ alkyl esters and methacrylic $C_1$-$C_4$ alkyl esters. Among these nonionogenic monomers, particular preference is given to acrylamide. As in the case of the homopolymers described above, these copolymers can also be crosslinked. A copolymer which is preferred according to the invention is the crosslinked acrylamide/methacryloyloxyethyltrimethylammonium chloride copolymer. Such copolymers, in which the monomers are present in a weight ratio of approximately 20:80, are commercially available as an approximately 50% strength nonaqueous polymer dispersion under the name Salcare® SC 92.

In another preferred embodiment, naturally occurring thickening agents are used. Preferred thickening agents of this embodiment are for example nonionic guar gums. According to the invention, both modified and unmodified guar gums can be used.

Unmodified guar gums are sold for example under the trade name Jaguar® C by the company Rhone Poulenc. Modified guar gums which are preferred according to the invention contain $C_1$-$C_6$ hydroxyalkyl groups. Preference is given to the groups hydroxymethyl, hydroxyethyl, hydroxypropyl and hydroxybutyl. Guar gums modified in this way are known in the prior art and can be prepared for example by reacting the guar gums with alkylene oxides. The degree of hydroxyalkylation, which corresponds to the number of consumed alkylene oxide molecules relative to the number of free hydroxyl groups in the guar gum, is preferably between 0.4 and 1.2. Guar gums modified in this way are commercially available under the trade names Jaguar® HP8, Jaguar® HP60, Jaguar® HP120, Jaguar® DC293 and Jaguar® HP105 from the company Rhone Poulenc.

Other suitable natural thickening agents are likewise already known from the prior art.

According to this embodiment, preference is also given to biosaccharide gums of microbial origin, such as scleroglucan gums or xanthan gums, gums from plant exudates, such as for example gum arabic, ghatti gum, karaya gum, tragacanth gum, carrageen gum, agar agar, carob seed grain, pectins, alginates, starch fractions and derivatives, such as amylose, amylopectin and dextrins, cellulose derivatives, such as for example methylcellulose, carboxyalkylcelluloses and hydroxyalkylcelluloses.

Preferred hydroxyalkylcelluloses are in particular the hydroxyethylcelluloses sold under the names Cellosize® by the company Amerchol and Natrosol® by the company Hercules. Suitable carboxyalkylcelluloses are in particular the carboxymethylcelluloses, such as those sold under the names Blanose® by the company Aqualon, Aquasorb® and Ambergum® by the company Hercules and Cellgon® by the company Montello.

Preference is also given to starch and derivatives thereof. Starch is a storage substance of plants which occurs primarily in tubers and roots, in cereal seeds and in fruits and can be obtained from a large number of plants in high yield. Polysaccharide, which is insoluble in cold water and forms a colloidal solution in boiling water, can be obtained for example from potatoes, cassava, sweet potato, maranta, corn, cereal, rice, legumes, such as for example peas and beans, bananas or the marrow of certain types of palm (for example sago palm). According to the invention, it is possible to use natural starches obtained from plants and/or chemically or physically modified starches. Modification can be achieved for example by introducing various functional groups onto one or more of the hydroxyl groups of the starch. These are usually esters, ethers or amides of starch having optionally substituted $C_1$-$C_{40}$ radicals. A corn starch etherified with a 2-hydroxypropyl group is particularly advantageous, as is sold for example by the company National Starch under the trade name Amaze®.

But also nonionic, fully synthetic polymers, such as for example polyvinyl alcohol, polyvinylpyrrolidinone, Preferred nonionic, fully synthetic polymers are sold for example by the company BASF under the trade name Luviskol®. Copolymers of butylene, ethylene and styrene or copolymers of propylene, ethylene and styrene are also particularly suitable for use as nonionic thickening agents according to the invention.

Besides their excellent thickening properties, such nonionic polymers also enable a significant improvement in the sensory feel of the resulting preparations.

Inorganic thickening agents which have proven to be particularly suitable in the context of the present invention are phyllosilicates (polymeric, crystalline sodium disilicates). Particular preference is given to clays, particularly magnesium aluminum silicate, such as for example bentonite, particularly smectites, such as montmorillonite or hectorite, which may optionally also be suitably modified, and synthetic phyllosilicates, such as for example the magnesium phyllosilicate sold by the company Süd Chemie under the trade name Optigel®.

The most suitable thickeners are thickeners from the group consisting of celluloses, hydroxy-C2-C6-alkylcelluloses, carboxymethylcelluloses, alginic acid, (meth)acrylate polymers and/or xanthan gum. It is therefore very particularly preferred to incorporate one or more thickeners from this group into the agent (b) according to the invention.

Particular preference is also given to a multicomponent packaging unit (kit-of-parts) which is characterized in that the agent (b) in container (B) additionally (b4) contains one or more thickeners from the group consisting of celluloses, hydroxy-C2-C6-alkylcelluloses, carboxymethylcelluloses, alginic acid, (meth)acrylate polymers and/or xanthan gum.

In another particularly preferred embodiment, the agent (b) is in the form of a clear gel formulation and therefore does not itself contain any fatty constituents.

By mixing the agent (a), which contains one or more fatty constituents (a2), with the preferably clear, gel-like agent (b), an emulsion is produced which may be in the form of an O/W emulsion.

Particular preference is also given to a multicomponent packaging unit (kit-of-parts) which is characterized in that the agent (b) in container (B) contains, based on the total weight of the agent (b), fatty constituents from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and/or silicone oils in a total amount of less than 2.5% by weight, preferably less than 1.0% by weight, more preferably less than 0.5% by weight and particularly preferably less than 0.1% by weight.

Particular preference is also given to a multicomponent packaging unit (kit-of-parts) which is characterized in that the agent (b) in container (B) contains, based on the total weight of the agent (b), fatty constituents from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters and/or hydrocarbons in a total amount of less than 2.5% by weight, preferably less than 1.0% by weight, more preferably less than 0.5% by weight and particularly preferably less than 0.1% by weight.

The definitions of the fatty constituents correspond to the definitions of the fatty constituents (a2) in the agent (a).

Decoloration of Colored Keratin Fibers

The multicomponent packaging unit according to the invention is a system comprising the agents (a) and (b) which is used to decolor previously colored keratin fibers, in particular human hair. The colored keratin fibers are usually fibers which have been previously colored using conventional oxidation dyes and/or substantive dyes known to the person skilled in the art.

The decoloring agents are suitable for removing colors that have been produced on the keratin fibers using oxidation dyes based on developer and coupler components. If the following compounds have been used as developers, the colors produced thereby can be removed in a satisfactory and effective manner, and without any subsequent darkening, by using the decoloring agent: p-phenylenediamine, p-toluylenediamine-N,N-bis-(β-hydroxyethyl)-p-phenylenediamine, 4-N,N-bis-(β-hydroxyethyl)amino-2-methylaniline, 2-(β-hydroxyethyl)-p-phenylenediamine, 2-(α,β-dihydroxyethyl)-p-phenylenediamine, 2-hydroxymethyl-p-phenylenediamine, bis-(2-hydroxy-5-aminophenyl) methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)pyrazole.

If the following compounds have been used as couplers, the colors produced thereby can also be removed with a very good decoloration result: m-phenylenediamine derivatives, naphthols, resorcinol and resorcinol derivatives, pyrazolones and m-aminophenol derivatives. Suitable coupler substances are in particular 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

1-Naphthol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

The substrate to be decolored may also have been colored using substantive dyes. As substantive dyes, mention may be made in particular of nitrophenylenediamines, nitroaminophenols, azo dyes, anthraquinones or indophenols. Preferred substantive dyes are the compounds known under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

Furthermore, the substrates to be decolored may also be colored using natural dyes occurring in nature, such as those contained for example in henna red, henna neutral, henna black, chamomile blossom, sandalwood, black tea, buckthorn bark, salvia, logwood, madder root, catechu, Spanish cedar and alkanna root.

The decoloring agents according to the invention are conceived for removing these colorings and therefore preferably do not themselves contain any dyes, that is to say any oxidation dye precursors of the developer type and of the coupler type, and also do not contain any substantive dyes.

In another preferred embodiment, therefore, a multicomponent packaging unit (kit-of-parts) according to the invention is characterized in that the total amount of all dyes and oxidation dye precursors contained in the agent (a) is at most 0.2% by weight, preferably at most 0.1% by weight, more preferably at most 0.05% by weight and particularly preferably at most 0.01% by weight, based on the total weight of the agent (a), and the total amount of all dyes and oxidation dye precursors contained in the agent (b) is at most 0.2% by weight, preferably at most 0.1% by weight, more preferably at most 0.05% by weight and particularly preferably at most 0.01% by weight, based on the total weight of the agent (b).

The multicomponent packaging unit according to the invention is used for reductive decoloration of colored keratin fibers. The agents (a) and (b) together form the ready-to-use decoloring agent, which contains a reducing agent. For reasons of incompatibility and to avoid exothermic, uncontrollable reactions, the agents (a) and (b) therefore preferably contain no oxidizing agent.

Here, oxidizing agents will be understood to mean in particular the oxidizing agents which can also be used for oxidative decoloration, such as for example hydrogen peroxide and persulfates (potassium persulfate (alternatively potassium peroxodisulfate), sodium persulfate (sodium peroxodisulfate) and ammonium persulfate (alternatively ammonium peroxodisulfate)). Preferably, therefore, neither of the agents (a) and (b) contains the aforementioned oxidizing agents.

In another preferred embodiment, therefore, a multicomponent packaging unit (kit-of-parts) according to the invention is characterized in that the total amount of all oxidizing agents from the group consisting of peroxides and persulfates contained in the agent (a) is at most 0.2% by weight, preferably at most 0.1% by weight, more preferably at most 0.05% by weight and particularly preferably at most 0.01% by weight, based on the total weight of the agent (a), and the total amount of all oxidizing agents from the group consisting of peroxides and persulfates contained in the agent (b) is at most 0.2% by weight, preferably at most 0.1% by weight, more preferably at most 0.05% by weight and particularly preferably at most 0.01% by weight, based on the total weight of the agent (b).

The agents (a) and (b) according to the invention may also contain further active substances, auxiliaries and additives, such as for example nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)/polyoxyalkylene(B) block copolymers, grafted silicone polymers; cationic polymers such as quaternized cellulose ethers, polysiloxanes having quaternary groups, dimethyldiallyl ammonium chloride polymers, acrylamide/dimethyldiallyl ammonium chloride copolymers, dimethylaminoethyl methacrylate/vinylpyrrolidinone copolymers quaternized with diethyl sulfate, vinylpyrrolidone/imidazolinium methochloride copolymers and quaternized polyvinyl alcohol; zwitterionic and amphoteric polymers; anionic polymers such as for example polyacrylic acids or crosslinked polyacrylic acids; structuring agents such as glucose, maleic acid and lactic acid, hair-conditioning compounds such as phospholipids, for example lecithin and cephalins; perfume oils, dimethyl isosorbide and cyclodextrins; active substances for improving the fiber structure, in particular mono-, di- and oligosaccharides, such as for example glucose, galactose, fructose, fruit sugars and lactose; colorants for coloring the agent; anti-dandruff substances such as piroctone olamine, zinc omadine and climbazole; amino acids and oligopeptides; animal- and/or plant-based protein hydrolysates, as well as in the form of the fatty acid condensation products or optionally anionically or cationically modified derivatives thereof, vegetable oils; light stabilizers and UV blockers; active substances such as panthenol, pantothenic acid, pantolactone, allantoin, pyrrolidinonecarboxylic acids and salts thereof, as well as bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, pro-vitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments and also propellants such as propane/butane mixtures, $N_2O$, dimethyl ether, $CO_2$ and air. In this connection, reference is expressly made to the known monographs, for example Kh. Schrader, Grundlagen und Rezepturen der Kosmetika, 2nd edition, Hüthig Buch Verlag, Heidelberg, 1989, which reflect the relevant knowledge of the person skilled in the art.

As already described above, the ready-to-use decoloring agent is produced by mixing the agents (a) and (b). In principle, the agents (a) and (b) may be mixed in different mixing ratios, such as for example (a)/(b) of 20:1 to 1:20.

The agent (a) is preferably a solid, pulverulent, in particular preferably paste-like agent. In order that said agent can also be completely solubilized when mixed with the agent (b), however, it is advantageous to use the agent (b) at least in the same amount as the agent (a). It is also preferred to use the agent (b) in an excess.

In another preferred embodiment, a multicomponent packaging unit according to the invention is therefore characterized in that the amounts of the agent (a) in container (A) and of the agent (b) in container (B) are selected so that, when preparing the application mixture, that is to say when mixing the agents (a) and (b), the mixing ratio (a)/(b) is from 1:5 to 5:1, preferably 1:3 to 3:1, more preferably 1:2 to 2:1.

To prepare the mixture, for example the agent (a) from container (A) may be fully transferred into container (B), which already contains the agent (b). In this case, the size of the container (B) is selected so that the container (B) can hold the total amount of the agents (a) and (b) and also enables a mixing of the two agents (a) and (b), for example by shaking or stirring.

Analogously, the mixture may also be prepared by fully transferring the agent (b) from container (B) into container (A), which already contains the agent (a). In this case, the size of the container (A) is selected so that the container (A) can hold the total amount of the agents (a) and (b) and also enables a mixing of the two agents (a) and (b), for example by shaking or stirring.

Another possibility for preparing the application mixture is to fully transfer the two agents (a) and (b) from the containers (A) and (B) into a third container (C), which then enables the mixing of the two agents (a) and (b), for example by shaking or stirring.

Example: A Multicomponent Packaging Unit According to the Invention Contains 25 g of the agent (a) in container (A)
100 g of the agent (b) in container (B)
In order to prepare the application mixture, the agent (b) is fully transferred from container (B) into container (A). The agents (a) and (b) are then shaken or stirred. The mixing ratio of the agents (a)/(b) is (25 g/100 g)=0.25.

Example: A Multicomponent Packaging Unit According to the Invention Contains 100 g of the agent (a) in container (A)
100 g of the agent (b) in container (B)
In order to prepare the application mixture, the agent (b) is fully transferred from container (B) into container (A). The agents (a) and (b) are then shaken or stirred. The mixing ratio of the agents (a)/(b) is (100 g/100 g)=1.0.

The multicomponent packaging unit according to the invention may additionally also contain one or more further agents in further separately presented containers. By way of example, the multicomponent packaging unit according to the invention may also comprise a container (C) containing a cosmetic agent (c). The agent (c) may be for example a pretreatment agent, an aftertreatment agent or a care agent.

Method

The above-described multicomponent packaging unit (kit-of-parts) according to the invention can be used in methods for reductive decoloration.

A second subject matter of the present invention is a method for reductive decoloration of colored keratin fibers, comprising the following steps in the specified order (I) preparing a ready-to-use decoloring agent by mixing an agent (a) with an agent (b), wherein
   the agent (a) is an agent of the first subject matter, as described in detail above,
   the agent (b) is an agent of the first subject matter, as likewise described in detail above,
(II) applying the ready-to-use decoloring agent to colored keratin fibers,
(III) leaving the decoloring agent to act for a period of 5 to 60 minutes, preferably 10 to 55 minutes, more preferably 20 to 50 minutes and particularly preferably 30 to 45 minutes,
(IV) rinsing off the decoloring agent from the keratin fibers,
(V) optionally applying an aftertreatment agent to the keratin fibers, wherein the aftertreatment agent contains at least one amphoteric, zwitterionic and/or anionic surfactant,
(VI) optionally rinsing off the aftertreatment agent from the keratin fibers.

Steps (I), (II), (III) and (IV) of the method represent the procedure for decoloring the keratin fibers and are accordingly carried out in direct temporal succession. There is in principle no time limit for the period between steps (IV) and (V). For instance, step (V) may take place hours, days or for example even up to two weeks after the end of step (IV).

It is likewise possible and in accordance with the invention if the decoloring steps (I) to (IV) are carried out multiple times in succession.

As described above, the agents (a) and (b) are preferably used in a quantity ratio (a)/(b) of preferably from 1:5 to 5:1, more preferably 1:3 to 3:1 and particularly preferably 1:2 to 2:1.

Preference is therefore also given to a method for decoloring colored keratin fibers which is characterized in that the preparation of the ready-to-use decoloring agent in step (I) takes place by mixing the agent (a) with the agent (b), the two agents being used in a quantity ratio (a)/(b) of from 1:5 to 5:1, more preferably 1:3 to 3:1 and particularly preferably 1:2 to 2:1.

The aftertreatment agent which can optionally be used in method steps (V) and (VI) may be for example a shampoo, a conditioner, a gel or a solution.

An aftertreatment agent may be used in particular to prevent any redarkening or reoxidation which may occur due to the effect of atmospheric oxygen on the decolored keratin fibers. To effectively prevent this reoxidation, the aftertreatment should take place before the atmospheric oxygen has time to act on the reduced keratin fibers. For this reason, the aftertreatment should where possible take place directly after the decoloration (that is to say in time terms immediately after method step (IV) has been completed). It is therefore preferred if there is a time period of at most 12 hours, preferably at most 6 hours, more preferably at most 1 hour and particularly preferably at most 30 minutes between the end of method step (IV) and the start of method step (V).

A preferred method according to the invention is thus characterized in that there is a time period of at most 12 hours, preferably at most 6 hours, more preferably at most 1 hour and particularly preferably at most 30 minutes between method steps (IV) and (V).

The application of the aftertreatment agent may also be repeated multiple times, for example if the aftertreatment agent is a shampoo which is applied regularly after the decoloration. If the aftertreatment, that is to say the performance of steps (V) to (VII), is repeated, it is possible to suppress the reoxidation for a particularly long period of time.

Particular preference is therefore given to a method for reductive decoloration of colored keratin fibers, comprising the following steps in the specified order (I) preparing a ready-to-use decoloring agent by mixing an agent (a) with an agent (b), wherein the agent (a) is an agent as defined in the description of the first subject matter, and the agent (b) is an agent as defined in the description of the first subject matter,
(II) applying the ready-to-use decoloring agent to colored keratin fibers,
(III) leaving the decoloring agent to act for a period of 5 to 60 minutes, preferably 10 to 55 minutes, more preferably 20 to 50 minutes and particularly preferably 30 to 45 minutes,
(IV) rinsing off the decoloring agent from the keratin fibers,
(V) applying an aftertreatment agent to the keratin fibers, wherein the aftertreatment agent contains at least one amphoteric, zwitterionic and/or anionic surfactant,
(VI) rinsing off the aftertreatment agent from the keratin fibers.
(VII) applying an aftertreatment agent to the keratin fibers, wherein the aftertreatment agent contains at least one amphoteric, zwitterionic and/or anionic surfactant,
(VIII) rinsing off the aftertreatment agent from the keratin fibers.

To prevent reoxidation or redarkening, the aftertreatment agent applied in method step (V) preferably additionally contains at least one acid from the group consisting of citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, maleic acid, succinic acid and/or oxalic acid.

A particularly preferred method for reductive decoloration of colored keratin fibers is therefore also characterized in that the aftertreatment agent applied in method step (V) contains at least one acid from the group consisting of citric acid, tartaric acid, malic acid, lactic acid, acetic acid, hydroxyethane-1,1-diphosphonic acid, methanesulfonic acid, malonic acid, maleic acid, fumaric acid, benzoic acid, hydrochloric acid, sulfuric acid, phosphoric acid, malonic acid, maleic acid and/or oxalic acid.

In other words, very particularly preference is therefore also given to a method for reductive decoloration of colored keratin fibers, comprising the following steps in the specified order (I) preparing a ready-to-use decoloring agent by mixing an agent (a) with an agent (b), wherein the agent (a) is an agent as defined in the description of the first subject matter, and the agent (b) is an agent as defined in the description of the first subject matter,
(II) applying the ready-to-use decoloring agent to colored keratin fibers,
(III) leaving the decoloring agent to act for a period of 5 to 60 minutes, preferably 10 to 55 minutes, more preferably 20 to 50 minutes and particularly preferably 30 to 45 minutes,
(IV) rinsing off the decoloring agent from the keratin fibers, (V) applying an aftertreatment agent to the keratin fibers, wherein the aftertreatment agent
  contains at least one acid from the group consisting of citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, maleic acid and/or oxalic acid, and
(VI) rinsing off the aftertreatment agent from the keratin fibers.

What has been stated above in relation to the agent according to the invention applies, mutatis mutandis, to other preferred embodiments of the method according to the invention.

EXAMPLES 1.1. Coloration

The following formulations were prepared (all figures stated in % by weight):

Coloring Cream (F1)

| Raw material | % by weight |
| --- | --- |
| Cetearyl alcohol | 8.5 |
| C12-C18 fatty alcohols | 3.0 |
| Ceteareth-20 | 0.5 |
| Ceteareth-12 | 0.5 |
| Plantacare 1200 UP (lauryl glucoside, 50-53% strength aqueous solution) | 2.0 |
| Sodium laureth-6 carboxylate (21% strength aqueous solution) | 10.0 |
| Sodium myreth sulfate (68-73% strength aqueous solution) | 2.8 |
| Sodium acrylate, trimethylammoniopropylacrylamide chloride copolymer (19-21% strength aqueous solution) | 3.8 |
| Potassium hydroxide | 0.83 |
| p-Toluylenediamine, sulfate | 2.25 |
| m-Aminophenol | 0.075 |
| 2-Amino-3-hydroxypyridine | 0.12 |
| Resorcinol | 0.62 |
| 4-Chlororesorcinol | 0.26 |
| 3-Amino-2-methylamino-6-methoxypyridine | 0.04 |
| 1,3-Bis(2,4-diaminophenoxy)propane, tetrahydrochloride | 0.05 |
| Ammonium sulfate | 0.1 |
| Sodium sulfite | 0.4 |
| Ascorbic acid | 0.1 |
| 1-Hydroxyethane-1,1-diphosphonic acid (60% strength aqueous solution) | 0.2 |
| Ammonia (25% strength aqueous solution) | 7.2 |
| Water | to 100 |

Oxidizing Agent (Ox)

| Raw material | % by weight |
| --- | --- |
| Sodium benzoate | 0.04 |
| Dipicolinic acid | 0.1 |
| Disodium pyrophosphate | 0.1 |
| Potassium hydroxide | 0.09 |
| 1,2-Propylene glycol | 1.0 |
| 1-Hydroxyethane-1,1-diphosphonic acid (60% strength aqueous solution) | 0.25 |
| Liquid paraffin | 0.30 |
| Steartrimonium chloride | 0.39 |
| Cetearyl alcohol | 3.4 |
| Ceteareth-20 | 1.0 |
| Hydrogen peroxide (50% strength aqueous solution) | 12.0 |

The coloring cream (F1) and the oxidizing agent (Ox) were mixed in a quantity ratio of 1:1 and were applied to hair strands (Kerling Euronaturhaar, white). The weight ratio of application mixture:hair was 4:1, and the leave-in time was 30 minutes at a temperature of 32 degrees Celsius. The strands were then rinsed with water, dried and left to rest at room temperature for at least 24 hours. The strands were colored in a dark brown shade.

The hair was analyzed colorimetrically, and the L value was determined.

1.2. Decoloration

The following decoloring agents were prepared (all figures stated in % by weight active substance):

Agent (a)

| Agent (a) | Comparison (aV) | Invention (aE) |
| --- | --- | --- |
| Versagel M 1600 [1] | 7.6 | 7.6 |
| Lanette N [2] | 10.8 | 10.8 |
| Ceteareth-20 (C16-C18 fatty alcohol, ethoxylated with 20 EO) | 0.9 | 0.9 |
| Ceteareth-50 (C16-C18 fatty alcohol, ethoxylated with 50 EO) | 5.0 | 5.0 |
| Formamidinesulfinic acid | — | 10.0 |
| Sodium dithionite | 10.0 | — |
| Liquid paraffin | to 100 | to 100 |

[1] INCI: Liquid Paraffin (Mineral Oil), ethylene/propylene/styrene copolymer, butylene/ethylene/-styrene copolymer
[2] INCI: Cetearyl alcohol (approximately 90%) and sodium cetearyl sulfate (approximately 10.0%)

Agent (b)

| Agent (b) | (b1) | (b2) |
| --- | --- | --- |
| Natrosol 250 HR (hydroxyethylcellulose) | — | 2.0 |
| Monoethanolamine | 1.0 | 1.0 |
| Emulgade F [3] | 3.0 | — |
| Water (distilled) | to 100 | to 100 |

[3] CETEARYL ALCOHOL, PEG-40 CASTOR OIL, SODIUM CETEARYL SULFATE

The agents (aV) and (b1) were stirred together in a quantity ratio (aV)/(b1) of 1:1 (that is to say 100 g of agent (aV) and 100 g of agent (b1)). The two agents were able to be mixed together without any dust being produced.

The agents (aE) and (b1) were stirred together in a quantity ratio (aE)/(b1) of 1:1 (that is to say 100 g of agent (aE) and 100 g of agent (b1)). The two agents were able to be mixed together without any dust being produced.

The ready-to-use decoloring agents thus prepared were each applied to the hair colored per point 1.1 and were left to act for 30 minutes at a temperature of 20° C. The strands were then rinsed with water for 20 seconds and dried.

The hair was again analyzed colorimetrically, and the L value was determined.

To determine the decoloring effect, the $\Delta L$ value was determined according to the following formula.

$$\Delta L = L(\text{after decoloration}) - L(\text{after coloration})$$

Within the Lab color space, the L-axis describes the brightness of a color (L=0 means black, L=100 means white). The greater the $\Delta L$ value, the greater the difference in the brightness of the color and the greater the hair has been decolored. The higher the $\Delta L$ value, the more effective a decoloring agent.

| | L value prior to decoloration | L value after decoloration | ΔL |
|---|---|---|---|
| (aV) + (b1) | 24.7 | 34.3 | 9.6 |
| (aE) + (b1) | 24.7 | 42.7 | 18.0 |

Analogously, the agents (aV) and (b2) were stirred together in the quantity ratio (aV)/(b2) of 1:1 (that is to say 100 g of agent (aV) and 100 g of agent (b2)) and were applied. The two agents were able to be mixed together without any dust being produced. The decoloration took place as described above.

Analogously, the agents (aE) and (b2) were stirred together in the quantity ratio (aE)/(b2) of 1:1 (that is to say 100 g of agent (aE) and 100 g of agent (b2)) and were applied. The two agents were able to be mixed together without any dust being produced. The decoloration took place as described above.

| | L value prior to decoloration | L value after decoloration | ΔL |
|---|---|---|---|
| (aV) + (b2) | 24.5 | 33.0 | 8.5 |
| (aE) + (b2) | 24.5 | 43.1 | 18.6 |

1.3. Aftertreatment

The hair strands decolored in point 1.2. were treated with the following aftertreatment agents N1 to N6.

Aftertreatment Agents (N) (all Figures Stated in % by Weight)

| | N1 | N2 | N3 |
|---|---|---|---|
| Cetearyl alcohol | 2.25 | 5.00 | 2.25 |
| Sodium cetearyl sulfate | 0.30 | 0.70 | 0.30 |
| PEG-40 hydrogenated castor oil | 0.30 | 1.00 | 0.30 |
| Citric acid | 0.05 | — | 0.05 |
| Oxalic acid | 1.50 | 1.30 | — |
| Succinic acid | — | — | 1.60 |
| Sulfuric acid (20% strength aqueous solution) | — | — | 0.60 |
| Monoethanolamine | 0.60 | 0.50 | — |
| Water | to 100 | to 100 | to 100 |

| | N4 | N5 | N6 |
|---|---|---|---|
| Cetearyl alcohol | 2.00 | 4.50 | 4.50 |
| Sodium cetearyl sulfate | 0.50 | 0.60 | 0.60 |
| PEG-40 hydrogenated castor oil | 0.40 | 0.60 | 0.60 |
| Succinic acid | — | — | 1.80 |
| Malic acid | 1.80 | — | — |
| Oxalic acid | — | 2.50 | — |
| Sulfuric acid (20% strength aqueous solution) | 0.50 | — | — |
| Monoethanolamine | — | — | 0.20 |
| Water | to 100 | to 100 | to 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A multicomponent packaging unit (kit-of-parts) for reductive decoloration of colored keratin fibers, which comprises, presented separately from one another,
   a container (A) containing a cosmetic agent (a) and
   a container (B) containing a cosmetic agent (b),
   wherein
   the agent (a) in container (A)
   (a1) includes one or more sulfinic acid derivatives selected from the group consisting of
   $(H_2N)(NH)C(SO_2H)$, formamidinesulfinic acid;
   $HN(CH_2SO_2Na)_2$, disodium [(sulfinatomethyl)amino]methanesulfinate;
   $HN(CH_2SO_2K)_2$, dipotassium [(sulfinatomethyl)amino]methanesulfinate;
   $HN(CH_2SO_2H)_2$, [(sulfinomethyl)amino]methanesulfinic acid;
   $N(CH_2SO_2Na)_3$, trisodium [bis(sulfinatomethyl)amino]methanesulfinate;
   $N(CH_2SO_2K)_3$, tripotassium [bis(sulfinatomethyl)amino]methanesulfinate;
   $N(CH_2SO_2H)_3$, [bis(sulfinomethyl)amino]methanesulfinic acid;
   $H_2NCH(CH_3)SO_2Na$, sodium 1-aminoethane-1-sulfinate;
   $H_2NCH(CH_3)SO_2K$, potassium 1-aminoethane-1-sulfinate;
   $H_2NCH(CH_3)SO_2H$, 1-aminoethane-1-sulfinic acid;
   $HN(CH(CH_3)SO_2Na)_2$, disodium 1-[(1-sulfinatoethyl)amino]ethane-1-sulfinate;
   $HN(CH(CH_3)SO_2K)_2$, dipotassium 1-[(1-sulfinatoethyl)amino]ethane-1-sulfinate;
   $HN(CH(CH_3)SO_2H)_2$, 1-[(1-sulfinoethyl)amino]ethane-1-sulfinic acid;
   $N(CH(CH_3)SO_2Na)_3$, trisodium 1-[bis(1-sulfinatoethyl)amino]ethane-1-sulfinate;
   $N(CH(CH_3)SO_2K)_3$, tripotassium 1-[bis(1-sulfinatoethyl)amino]ethane-1-sulfinate; and
   $N(CH(CH_3)SO_2H)_3$, 1-[bis(1-sulfinoethyl)amino]ethane-1-sulfinic acid;
   (a2) includes one or more nonionic fatty constituents in an amount of at least 10% by weight selected from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and silicone oils,
   (a3) has a water content of at most 10.0% by weight, based on the total weight of the agent (a),
   wherein (a) is a water-in-oil emulsion and (a) comprises less than 0.1 sulfites by weight based on the total weight of the agent (a);
   the agent (b) in container (B)
   (b1) has a water content of at least 30.0% by weight, based on the total weight of the agent (b); and
   (b2) one or more alkalizing agents selected from the group consisting of ammonia, alkanolamines and basic amino acids;
   wherein the agent (b) in container (B) has a pH of 7.5 to 12.5.

2. The multicomponent packaging unit (kit-of-parts) according to claim 1, characterized in that the agent (a) in container (A)
   (a1) contains $(H_2N)(NH)C(SO_2H)$ formamidinesulfinic acid as the sulfinic acid derivative.

3. The multicomponent packaging unit (kit-of-parts) according to claim 1, wherein the agent (a) in container (A) includes, based on the total weight of the agent (a), one or more sulfinic acid derivatives from the group (a1) in a total amount of 0.1 to 50.0% by weight.

4. The multicomponent packaging unit (kit-of-parts) according to claim 1, wherein the agent (a) in container (A) includes, based on the total weight of the agent (a), one or more nonionic fatty constituents from the group (a2) in a total amount of 10.0 to 90.0% by weight.

5. The multicomponent packaging unit (kit-of-parts) according to claim 1, wherein the agent (a) in container (A)
(a2) contains one or more hydrocarbons in a total amount of 15.0 to 90.0% by weight, based on the total weight of the agent (a).

6. The multicomponent packaging unit (kit-of-parts) according to claim 1, wherein the agent (a) in container (A)
(a3) has a water content of at most 8.0% by weight, based on the total weight of the agent (a).

7. The multicomponent packaging unit (kit-of-parts) according to claim 1, wherein the agent (a) in container (A) further includes
(a4) one or more nonionic surfactants in a total amount of 0.1 to 15.0% by weight, based on the total weight of the agent (a).

8. The multicomponent packaging unit (kit-of-parts) according to claim 1, wherein the agent (a) in container (A) further includes
(a5) one or more nonionic polymers in a total amount of 0.1 to 15.0% by weight, based on the total weight of the agent (a).

9. The multicomponent packaging unit (kit-of-parts) according to claim 1, wherein the agent (b) in container (B)
(b1) has a water content of at least 40.0% by weight, based on the total weight of the agent (b).

10. The multicomponent packaging unit (kit-of-parts) according to claim 1, wherein the agent (b) in container (B) further includes
(b4) one or more thickeners selected from the group consisting of celluloses, hydroxy-C2-C6-alkylcelluloses, carboxymethylcelluloses, alginic acid, (meth)acrylate polymers and xanthan gum.

11. The multicomponent packaging unit (kit-of-parts) according to claim 1, wherein the agent (b) in container (B) further includes, based on the total weight of the agent (b), fatty constituents selected from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons, and silicone oils in a total amount of less than 2.5% by weight.

12. A multicomponent packaging unit (kit-of-parts) for reductive decoloration of colored keratin fibers, which comprises, presented separately from one another,
a container (A) containing a cosmetic agent (a) and
a container (B) containing a cosmetic agent (b),
wherein
the agent (a) in container (A)
(a1) includes one or more sulfinic acid derivatives selected from the group consisting of
$HN(CH_2SO_2Na)_2$, disodium [(sulfinatomethyl)amino]methanesulfinate;
$HN(CH_2SO_2K)_2$, dipotassium [(sulfinatomethyl)amino]methanesulfinate;
$HN(CH_2SO_2H)_2$, [(sulfinomethyl)amino]methanesulfinic acid;
$N(CH_2SO_2Na)_3$, trisodium [bis(sulfinatomethyl)amino]methanesulfinate;
$N(CH_2SO_2K)_3$, tripotassium [bis(sulfinatomethyl)amino]methanesulfinate;
$N(CH_2SO_2H)_3$, [bis(sulfinomethyl)amino]methanesulfinic acid;
$H_2NCH(CH_3)SO_2Na$, sodium 1-aminoethane-1-sulfinate;
$H_2NCH(CH_3)SO_2K$, potassium 1-aminoethane-1-sulfinate;
$H_2NCH(CH_3)SO_2H$, 1-aminoethane-1-sulfinic acid;
$HN(CH(CH_3)SO_2Na)_2$, disodium 1-[(1-sulfinatoethyl)amino]ethane-1-sulfinate;
$HN(CH(CH_3)SO_2K)_2$, dipotassium 1-[(1-sulfinatoethyl)amino]ethane-1-sulfinate;
$HN(CH(CH_3)SO_2H)_2$, 1-[(1-sulfinoethyl)amino]ethane-1-sulfinic acid;
$N(CH(CH_3)SO_2Na)_3$, trisodium 1-[bis(1-sulfinatoethyl)amino]ethane-1-sulfinate;
$N(CH(CH_3)SO_2K)_3$, tripotassium 1-[bis(1-sulfinatoethyl)amino]ethane-1-sulfinate; and
$N(CH(CH_3)SO_2H)_3$, 1-[bis(1-sulfinoethyl)amino]ethane-1-sulfinic acid;
(a2) includes one or more nonionic fatty constituents in an amount of at least 10% by weight selected from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, $C_{12}$-$C_{30}$ fatty acid esters, hydrocarbons and silicone oils,
(a3) has a water content of at most 10.0% by weight, based on the total weight of the agent (a),
wherein (a) is a water-in-oil emulsion and (a) comprises less than 0.1 sulfites by weight based on the total weight of the agent (a);
the agent (b) in container (B)
(b1) has a water content of at least 30.0% by weight, based on the total weight of the agent (b); and
(b2) one or more alkalizing agents selected from the group consisting of ammonia, alkanolamines and basic amino acids;
wherein the agent (b) in container (B) has a pH of 7.5 to 12.5.

13. A method for reductive decoloration of colored keratin fibers, including the following steps in the specified order:
(I) preparing a ready-to-use decoloring agent by mixing an agent (a) with an agent (b), wherein the agents (a) and (b) are defined in claim 1,
(II) applying the ready-to-use decoloring agent to colored keratin fibers,
(III) leaving the decoloring agent to act for a period of 5 to 60 minutes,
(IV) rinsing off the decoloring agent from the keratin fibers,
(V) optionally applying an aftertreatment agent to the keratin fibers, wherein the aftertreatment agent contains at least one amphoteric, zwitterionic and/or anionic surfactant, and
(VI) optionally rinsing off the aftertreatment agent from the keratin fibers.

14. The method according to claim 13, wherein the aftertreatment agent applied in step (V) includes at least one acid selected from the group consisting of citric acid, tartaric acid, malic acid, lactic acid, acetic acid, hydroxyethane-1, 1-diphosphonic acid, methanesulfonic acid, malonic acid, maleic acid, fumaric acid, benzoic acid, hydrochloric acid, sulfuric acid, phosphoric acid, malonic acid, maleic acid, succinic acid, and oxalic acid.

* * * * *